United States Patent [19]

Giroldini

[11] Patent Number: 4,487,952

[45] Date of Patent: Dec. 11, 1984

[54] PREPARING CARBAMIC ACID ESTERS

[75] Inventor: Villiam Giroldini, Milan, Italy

[73] Assignee: Anic S.p.A., Palermo, Italy

[21] Appl. No.: 463,555

[22] Filed: Feb. 3, 1983

[30] Foreign Application Priority Data

Feb. 9, 1982 [IT] Italy ................ 19519 A/82

[51] Int. Cl.$^3$ ............... C07C 125/063; C07C 125/07
[52] U.S. Cl. ..................................... 560/24; 560/25; 560/29; 560/30; 560/32; 260/465 D
[58] Field of Search ................ 560/24, 25, 29, 30, 560/32; 260/465 D

[56] References Cited

U.S. PATENT DOCUMENTS 3,895,054  7/1975  Zajacek et al. ............. 560/24 X
3,956,360  5/1976  Zajacek et al. ............. 560/24 X Primary Examiner—Bernard Helfin
Attorney, Agent, or Firm—Hedman, Gibson, Costigan & Hoare

[57] ABSTRACT

Process for the preparation of esters of carbamic acids by carbonylation of aromatic nitrocompounds, with carbon monoxide, in the presence of alcohols and of catalyst consisting of metallic selenides.

5 Claims, No Drawings

PREPARING CARBAMIC ACID ESTERS

This invention relates to a process having a high selectivity for producing esters of carbamic acids by carbonylation of aromatic nitrocompounds with carbon monoxide, in the presence of alcohols, which is characterized in that it employs metallic selenides as the catalysts.

Carbamates are compounds having a considerable commercial importance and find a direct application as plant medicaments or as intermediates for the synthesis of aromatic isocyanates such as Ph—NCO (Ph=phenyl) and $CH_3C_6H_3(NCO)_2$ obtained from the pyrolysis of the corresponding carbamates, Ph—NHCOOEt and $CH_3C_6H_3(NHCOOEt)_2$ (Et=ethyl).

Numerous synthesizing processes are known, viz.:

(a) Reaction of an isocyanate with an alcohol:

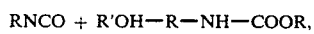

a synthesis which requires the use of isocyanates, which are both expensive and toxic starting materials.

(b) Direct carbonylation of nitrocompounds in the presence of alcohols, with a number of catalytic systems such as couples of metallic chlorides (Rh and Fe chlorides, Brit. Pat. No. 1 087 896) or mixtures of palladium chloride in the presence of a complex of ferrous chloride and pyridine (U.S. Pat. No. 4,178,455), or, in general, a salt of a metal of the palladium group in the presence of Lewis' acids and a tertiary amine (Belg. Pat. No. 837.563). These processes are impaired by the shortcoming of using catalysts based on vary expensive metals (rhodium and palladium) so that there are recovery problems for said metals, and also problems of selectivity of the reaction exist, because considerable amounts of by-products are originated, such as aromatic amines and ureas.

(c) Reaction between an aromatic amine, alcohols and carbon oxysulphide in the presence of baryum molybdate, thus with the use of toxic ingredients.

(c) Carbonylation of aromatic nitrocompounds directly with carbon monoxide, in the presence of alcohols, the catalysts being composed of elemental selenium and organic and inorganic bases (U.S. Pat. No. 3,956,360) which requires the adoption of rather drastic working conditions, such as temperatures between 160° C. and 200° C. and pressures of carbon monoxide comprised between 60 atm and 180 atm, in addition to the obligation of using amounts of selenium which are virtually stoichiometric relative to the nitrocompound, so that there are problems as to the recovery of selenium and purification of the end product.

It has now been found, and it is the subject matter of the present invention, that, by using a metallic selenide as the catalyst, it becomes possible to obtain an improved selectivity for the reaction in addition to having such conversion ratings that reduced amounts of selenium can be used, that is, actually catalytic quantities.

According to the present invention carbamic esters can be obtained, which have the general formula:

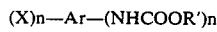

wherein Ar stands for an unsubstituted or heterocyclic aromatic nucleus, X indicates substituents on the aromatic ring, such as —H, —$CH_3$, —CHO, —$NR_2$, —CN, —OH, —COOH, —F, —Cl, —Br, —I. The value of n can be 1, 2 or 3. Moreover, R' indicates aliphatic and aralkyl radicals having from 1 to 16 carbon atoms, said radicals being straight-line, branched, cyclic, unsubstituted or substituted. The aromatic nitrocompounds used for the synthesis have a general formula $(X)nAr(NO_2)n$, X and n having the same meanings as explained in the foregoing. The alcohols used for the synthesis have the general formula R'—OH, R' having the same meaning as explained above. As examples of nitrocompounds and alcohols which lend themselves to the synthesis in question, the following can be listed: nitrobenzene, 2,4-binitrotoluene, p-nitroaniline, p-methoxynitrobenzene, p-chloronitrobenzene, p-methoxynitrobenzene, p.nitrophenol, alpha-nitronaphthalene and others, methyl alcohol, isopropanol, tert.butanol, benzyl alcohol, cyclohexyl alcohol and others.

The process according to the present invention is reduced to practice by reacting in an autoclave an appropriate mixture of the nitrocompound, the alcohol, the metallic selenide, carbon monoxide and an organic and/or inorganic base.

The reaction temperature varies from 100° C. to 200° C. and is preferably comprised between 140° C. and 180° C.

The pressure of the carbon monoxide, at the steady state temperature, may vary between 1 and 40 atm and is preferably comprised between 10 and 30 atm.

The metallic selenides useful as catalysts are selected from the group consisting of the following: CuSe, SnSe, $SnSe_2$, CoSe, NiSe, FeSe, VOSe, $V_2Se_3$, MnSe, $MoSe_3$, $Sb_2Se_3$, $Cr_2Se_3$, CdSe, $Bi_2Se_3$, $Ce_2Se_3$, $Ru_2Se_3$, $Rh_2Se_3$, PdSe, $PtSe_2$. A particularly pronounced catalytic activity is displayed by FeSe, VOSe, MnSe and SnSe.

It has been ascertained, furthermore, that the presence of iodide ions (I) in combintion with a few selenides (more particularly FeSe and VOSe) improves the reaction velocity by a factor of 2 and, moreover, it permits to work at lower temperatures, whereas the selectivity of the reaction is not modified.

The iodides employed to that purpose can be, for example, KI, NaI, LiI or iodides of organic bases.

The molar ratio of the catalyst to the nitrocompound varies from 1:200 to 1:20.

The organic and inorganic bases to be used as cocatalysts can be for example: triethylamine, pyridine, quinoline, sodium acetate, potassium acetate and others.

On completion of the reaction the catalyst is recovered by merely filtering it off from the reaction raw product and the product (the carbamate) is recovered by the conventional fractional distillation or fractional crystallization procedures.

It may be an advantage in order to improve the conversion rating, the kinetics and the selectivity of the reaction, to use two or more metallic selenides simultaneously as the catalysts. For example, the combinations FeSe+MnSe, FeSe+VOSe, MnSe+VOSe have proven useful. The ratio of either catalyst to the other can be varied between 1:10 and 10:1.

The main advantages of the use of the metallic selenides over the elemental selenium are the following:

(a) reduction of the amount of selenium in the catalytic system (b) considerable improvement in the reaction kinetics, which makes it possible to work under low carbon monoxide pressures and at moderate temperature, the advantage from the commercial standpoint being obvious.

(c) facilitated recovery and recycle of the catalyst, the latter having a less pronounced tendency to pass into homogeneous phase.

The ensuing examples illustrate the invention without limitation.

EXAMPLE 1

A 200-ml autoclave (approximate volume) is charged with 0.5 g (grams) of FeSe, 5 mls of pyridine, 10 mls of nitrobenzene (0.1 mol) and 40 mls of ethyl alcohol. The autoclave is heated to 170° C. with stirring and, as soon as the temperature is stabilized, carbon monoxide is introduced under the pressure of 30 atm. As the pressure drops to 23 atm, the gas is let off to a pressure of 9 atm, whereafter fresh carbon monoxide is introduced under the pressure of 30 atm. These operations are repeated as necessary. After 5.5 hours the autoclave is allowed to cool, the gases are bled off and the contents is GLC-analyzed (GLC=Gas Liquid Chromatography). The results are:

| Aniline | 0.3 mM (millimols) |
| Nitrobenzene | 45.2 mM |
| N—phenyl-ethylcarbamate | 51.5 mM |

The conversion is 55% and the selectivity is 98%. The catalyst is filtered off from the raw product of the reaction and the carbamate is purified by fractional distillation.

b.p.=120° C. under 6 mmHg (millimeters of mercury)
m.p.=52° C.

EXAMPLE 2

A 200-ml autoclave is charged with 0.5 g of VOSe, 5 mls pyridine, 10 mls nitrobenzene, 40 mls of ethyl alcohol. The autoclave is heated to 170° C. with stirring whereafter carbon monoxide is charged under a pressure of 30 atm, the procedure being the same as in Example 1. After 9 hours the autoclave is allowed to cool, vented and the contents is GLC-analyzed. The results are:

| Aniline | 6.7 mM |
| Nitrobenzene | 43.1 mM |
| N—phenyl-ethylcarbamate | 47.1 mM |

The conversion is 57% and the selectivity is 87.5%. The product is purified as in Example 1.

EXAMPLE 3

A 200-ml autoclave is charged with 0.5 g of SnSe, 5 mls pyridine, 13.7 g of p.nitrotoluene, 40 mls of ethyl alcohol. The autoclave is heated to 170° C. with stirring and charged with carbon monoxide under a pressure of 30 atm, the procedure being as described hereinbefore. After 8 hours the reaction is stopped and the contents of the autoclave are GLC-analyzed. There is obtained N-p.tolyl-ethylcarbamate=95 mM. Other by-products are p.toluidine and N,N-p.tolylurea. The conversion is 100% and the selectivity is 95%. The product is isolated from the raw material of the reaction upon evaporation of the solvent, by crystallization from hexane.

EXAMPLE 4

A 200-ml autoclave is charged with 0.95 g of MnSe, 5 mls of pyridine, 10 mls of nitrobenzene and 40 mls of ethyl alcohol. The autoclave is heated to 170° C. with stirring and charged with carbon monoxide under a pressure of 30 atm. After 4 hours, the reaction is stopped and the GLC-analysis of the raw product of the reaction gives the following results:

| Aniline | 0.8 mM |
| Nitrobenzene | 27.2 mM |
| N—phenyl-ethylcarbamate | 66.4 mM |

The conversion is 73% and the selectivity is 98%.

EXAMPLE 5

A 200-ml autoclave is charged with 0.5 g of FeSe, 0.61 g of KI, 5 mls of pyridine, 10 mls of nitrobenzene (0.1 mol) and 40 mls of $(CH_3)_2CHOH$. The autoclave is heated to 170° C. with stirring and then charged with carbon monoxide under a pressure of 30 atm. After 5 hours the reaction is over. The GLC-analysis gives the following results:

| Nitrobenzene | 0.0 |
| N—phenyl-isopropylcarbamate | 96 mM |

The conversion is 100% and the selectivity is 96%. The raw product, after that the catalyst is filtered off, is evaporated under a reduced pressure to remove pyridine and isopropyl alcohol. A solid crystalline residue is obtained, which is the raw carbamate. The product is purified by crystallization from toluene. N-phenyl-isopropylcarbamate has a m.p. of 87° C.–88° C.

EXAMPLE 6

A 200-ml autoclave is charged with 0.5 g of VOSe, 0.56 g of KI, 0.3 g of $CH_3COONa$, 5 mls of pyridine, 10 mls of nitrobenzene and 45 mls of ethyl alcohol. The autoclave is heated to a temperature of 170° C. with stirring and charged with carbon monoxide under a pressure of 30 atm. The reaction is completed within 2 hours. N-phenyl-ethylcarbamate is obtained with a selectivity of 88.6% and a conversion of 100%. The product is purified with the same procedure as in Example 1.

EXAMPLE 7

A 200-ml autoclave is charged with 0.5 g of FeSe, 0.56 g of KI, 5 mls of pyridine, 40 mls of ethanol, 13.9 g of p.nitrophenol (0.1 mol). The autoclave is heated to a temperature of 170° C. with stirring and charged with carbon monoxide under a pressure of 30 atm. After 4.5 hours the reaction is over. There are obtained 96 mM of N-p.hydroxyphenyl-ethylcarbamate. The conversion is 100% and the selectivity is 96%. The raw product of the reaction is filtered, the solvent evaporated off and the product is then isolated by crystallization from toluene.

EXAMPLE 8

A 200-ml steel autoclave is charged with 0.5 g of VOSe, 0.5 g of KI, 0.3 g of $CH_3COONa$, 5 mls of pyridine, 50 mls of ethanol and 18.2 g of 2,4-binitrotoluene (0.1 mol). The autoclave is heated to the temperature of 150° C., whereafter carbon monoxide is introduced under a pressure of 30 atm. After 4.5 hours the reaction is completed, the raw product of the reaction is filtered and the solvent is evaporated off. The residue is subjected to fractional crystallization from toluene-hexane. By so doing, there are isolated 19 g of tolyl-2,4-bis-diethylcarbamate. The conversion is 100% and the selectivity is 72%.

EXAMPLE 9

A 200-ml autoclave is charged with 0.5 g of FeSe, 0.6 g of KI, 5 mls of pyridine, 40 mls of ethanol and 15.3 g of p.methoxynitrobenzene (0.1 mol). The autoclave is heated to the temperature of 170° C. and then charged with carbon monoxide under a pressure of 30 atm. The reaction is completed after 2.5 hours. In the raw product of the reaction there are determined, by GLC (Gas-Liquid Chromatography) 95 mM of N-p.methoxyphenyl-ethylcarbamate. The conversion is 100% and the selectivity is 95%. The solvent is evaporated off from the raw product of the reaction, whereafter the product is purified by extraction and crystallization with hexane-toluene.

EXAMPLE 10

A 200-ml autoclave is charged with 0.5 g of VOSe, 0.25 g of CH₃COONa, 0.5 g of KI, 5 mls of pyridine, 45 mls of ethyl alcohol and 15.75 g of p.chloronitrobenzene (0.1 mol). The autoclave is heated to 170° C. and then charged with carbon monoxide under a pressure of 25 atm. After 7 hours the reaction is over. The GLC-analysis of the raw product of the reaction indicates the occurrence of:

| | |
|---|---|
| N,N—p. dichlorobiphenylurea | 2 mM |
| p. chloronitrobenzene | 18 mM |
| N—p. chlorophenyl-ethylcarbamate | 78 mM |

The conversion is 78% and the selectivity is 95%. The solvent is evaporated off from the reaction raw product whereafter the unreacted p.chloronitrobenzene is distilled off under reduced pressures. The residue is fractionally crystallized from hexane thus obtaining the pure carbamate.

I claim:

1. A process for the preparation of esters of carbamic acids comprising the step of reacting aromatic nitrocompounds with carbon monoxide in the presence of alcohols and catalysts selected from the group consisting of iron selenide, tin selenide, manganese selenide, vanadyl selenide and mixtures thereof and a cocatalyst comprising potassium iodide and pyridin as a reaction temperature between 100° C. and 200° C. and a pressure between 1 atm and 40 atm.

2. Process according to claim 1, characterized in that the reaction is carried out with molar ratios of the catalyst to the nitrocompound variable between 1:200 and 1:20.

3. Process according to claim 1, wherein the catalyst consists of a combination of two or more of the metallic selenides.

4. Process according to claim 3 wherein the catalyst is selected from the group consisting of FeSe and MnSe; FeSe and VOSe; or MnSe and VOSe.

5. Process according to claim 1, wherein the cocatalyst includes potassium acetate.

* * * * *